United States Patent [19]

Lewis

[11] 3,986,498
[45] Oct. 19, 1976

[54] REMOTE ECG MONITORING SYSTEM

[75] Inventor: David E. Lewis, Orange, Calif.

[73] Assignee: Videodetics Corporation, Anaheim, Calif.

[22] Filed: Sept. 8, 1975

[21] Appl. No.: 611,434

[52] U.S. Cl. .......................... 128/2.06 R; 128/2.1 A; 340/177 R
[51] Int. Cl.[2] ............................................. A61B 5/04
[58] Field of Search ................. 128/2.05 R, 2.06 G, 128/2.06 R, 2.1 A, 2.1 R; 340/177 R, 221; 178/DIG. 1; 179/2 DP, 2 TV; 325/31, 51, 37

[56] References Cited
UNITED STATES PATENTS

| 3,572,316 | 3/1971 | Vogglman et al. | 128/2.1 A |
| 3,603,881 | 9/1971 | Thornton | 128/2.1 A |
| 3,613,669 | 10/1971 | Corbin et al. | 128/2.1 A |
| 3,646,930 | 3/1972 | Patterson et al. | 128/2.1 A |

Primary Examiner—William E. Kamm
Attorney, Agent, or Firm—Philip M. Hinderstein

[57] ABSTRACT

A remote ECG monitoring and telemetry system for use in a hospital equipped with a master antenna television cable system comprising a portable patient sensor/transmitter unit for deriving ECG information and for transmitting a first frequency signal modulated with the ECG information; a receiver/transmitter unit positioned in the patient's room for receiving the first modulated signal and for coupling directly to the master antenna television cable a second frequency signal modulated with the ECG information; a converter/amplifier unit coupled to the master antenna television cable adjacent the head end thereof for receiving the second modulated signal and for coupling back into the master antenna television cable a high power, third frequency signal modulated with the ECG information; and a receiver/demodulator unit coupled to the master antenna television cable at a central monitoring station for receiving and demodulating the third modulated signal to derive the ECG information.

27 Claims, 5 Drawing Figures

REMOTE ECG MONITORING SYSTEM

BACKGROUND OF THE INVENTION

1. Field of the Inventions

The present invention relates to a remote ECG monitoring system and, more particularly, to a system for communicating ECG patient signals to monitors at convenient locations anywhere within a facility equipped with a master antenna television cable system.

2. Description of the Prior Art

Many patients in hospitals require constant monitoring of various, basic, life-support functions due to the critical nature of their physical condition. One of the most commonly monitored functions is a patient's electrocardiogram (ECG) signals and a patient in intensive care is typically equipped with a set of leads on his body and an ECG monitor right by his bedside.

In spite of the necessity for constantly watching the individual ECG monitors of all patients in an intensive care area, it is infeasible for a single nurse or trained ECG watcher to effectively watch an entire room full of monitors because of the physical space that each bed takes. Therefore, the typical solution to this problem is to provide a hard-wired connection between each ECG monitor positioned by the patient's bed and a plurality of slave monitors which are aligned in a series, in front of a console, at the nurse's station or some other convenient location. This permits a qualified nurse or ECG watcher to substantially and effectively monitor a number of patients at a single time.

Unfortunately, intensive care areas are either not large enough or too expensive to handle all patients requiring ECG monitoring. A variety of medical situations exist where doctors would like to be able to order an ECG monitor on a patient without having to subject the patient to the expense of intensive care. To achieve this, a portable monitor can be brought to the patient's room and connected to him, but now there is a problem of providing a qualified person to watch the monitor at all times. Since qualified people are very limited in number, this is an ineffective solution to the problem.

Another proposed solution is to use a form of telemetry. It has been proposed to place the ECG leads on the patient and to provide the patient with a transmitter which transmits radio waves containing the baseband ECG information. In order to receive these radio waves at a central monitoring station, it has been proposed to string antenna wires and amplifiers throughout the hospital to receive, amplify, and conduct the radio waves to the central monitoring station. Unfortunately, it is a relatively expensive procedure to modify the hospital to incorporate the antennas and amplifiers. Furthermore, because the Federal Communications Commission limits the amount of energy that may be transmitted, satisfactory performance requires substantial numbers of antennas and substantial amplification systems to derive a satisfactory signal at the receiver, and such systems provide for only a single receiver at a single location.

Still other problems exist with such a telemetry system. That is, since the patient's transmitted signal can be picked up wherever the antenna goes, it would not be possible to determine exactly where the patient is. Furthermore, the signals tend to fade in and out as the patient moves from place to place, into and out of close proximity to the antenna. Finally, if the patient is in his room and an emergency condition results, it is necessary to remove the leads from the patient and put a monitor on the patient because the existing transmitter does not have facility for a monitor.

SUMMARY OF THe INVENTION

According to the present invention, these problems are solved in a manner unknown heretofore. With the present remote monitoring system, a patient is provided with a portable transmitter unit which permits a certain freedom of movement in relation to a receiver unit which is mounted right in the patient's room to directly receive his transmitted signals. The transmitter has sufficient power and the receiver has sufficient sensitivity so that the patient can move around relatively freely without affecting receipt of the signal by the receiver. The receiver, in turn, after receiving the telemetry signal from the patient and demodulating it to provide the baseband information, provides an output plug which is adapted to receive a low-cost, non-isolated monitor which can be plugged in at any time to immediately view the patient's heartbeat, right in his room, without altering the patient's connections or hooking up something to him. Furthermore, the room receiver remodulates a power FM transmitter with the baseband information and applied it to the master antenna television cable, which already exists in the hospital to bring television signals to each patient's room. The carrier signal is chosen to be below the frequencies used by the television system, but well within the capability of the cable system, so that the signals may be readily carried by the cable.

Adjacent the head end of the CATV system, where all branch wires lead from, this signal is received, converted to some other frequency channel, amplified, and coupled back into the master antenna television cable. Once so inserted, this signal looks to the cable system just like any other carrier signal that might be coming from the roof antenna, i.e. it has the same basic strength and the same general frequency range, but on a non-interfering channel. With such an arrangement, one can go to any wall tap in the entire hospital and couple a receiver to the cable and receive and demodulate the signal which originated at any place else within the hospital. Furthermore, multiple monitors can be provided in different locations in the hospital for monitoring by different personnel.

With the present system, a trained nurse or ECG watcher can effectively monitor ECG and other patient information from widely scattered locations within a hospital at a single monitoring station. This being the case, it is unnecessary to put a patient in intensive care to monitor critical life-support functions. When a patient is in trouble, the nurse knows exactly where he is and a portable monitor can be immediately attached to his local receiver for monitoring instantaneous ECG information. The present system can be installed in a conventional hospital without any rewiring or modification thereof, other than the installation of the present equipment and the connection thereof to the conventional master antenna wall taps.

A plurality of receiver/monitors can be provided in a central nurse's station for monitoring simultaneously all patients. Furthermore, a chief cardiologist or other individual may have a single, tunable monitor in his office with provision for tuning in any one of the multiple patient stations. A patient unit and a receiver/retransmitter unit may be provided in the emergency room of the hospital so that a qualified watcher can view, from a central location, an ECG on a patient within a few minutes or seconds after the patient arrives in the emergency room. A patient unit and a receiver/retransmitter unit may also be provided in each operating room so that the anesthesiologist may obtain an opinion from a cardiologist without the cardiologist having to scrub up and come into the operating room to view the monitor the anesthesiologist is watching.

Briefly, the present remote monitoring and telemetry system for use in a facility equipped with a master antenna television cable system comprises a patient unit comprising: means for deriving baseband information from a patent; means for generating a first frequency signal; means for modulating said first frequency signal with said baseband information; and antenna means for transmitting said first modulated signal; a receiver/retransmitter unit comprising: means for receiving and demodulating said first modulated signal to derive said baseband information; means for generating a second frequency signal different from said first frequency signal; means for modulating said second frequency signal with said derived baseband information; and means for coupling said second modulated signal to said master antenna television cable; a converter/amplifier unit positioned adjacent the head end of said master antenna television cable comprising: means coupled to said master antenna television cable for receiving said second modulated signal; means operatively coupled to said receiving means for converting said second modulated signal to a third modulated signal having a frequency different from said second frequency; means for amplifying said third modulated signal; and means for coupling said amplified third modulated signal to said master antenna television cable; and a monitoring unit comprising; means coupled to said master antenna television cable for receiving and demodulating said third modulated signal to derive said baseband information.

OBJECTS

It is therefore an object of the present invention to provide a remote ECG monitoring system.

It is a further object of the present invention to provide a system for communicating ECG signals from a patient in a hospital to another point in the hospital where viewing is more convenient.

It is a still further object of the present invention to provide a remote ECG monitoring system for a hospital which utilizes the hospital's master antenna television cable.

It is another object of the present invention to provide a remote ECG monitoring system which eliminates the necessity for rewiring a hospital.

It is still another object of the present invention to provide a remote ECG monitoring system whereby ECG information can be simultaneously monitored at a variety of locations within a hospital.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like or corresponding parts in the several figures and wherein:

DESCRIPTION OF THE PREFERRED EMBODIMENT

Figure 1:
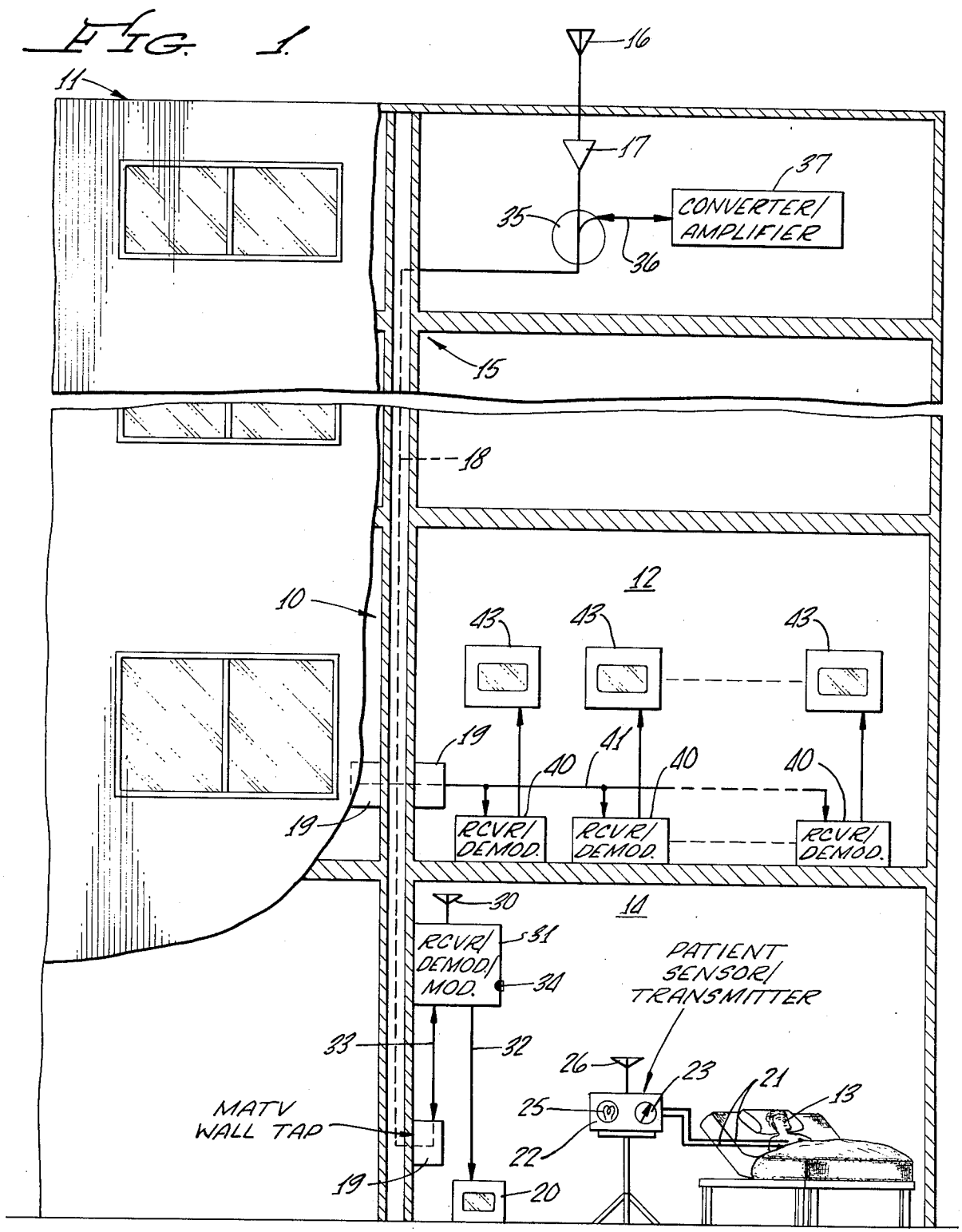
FIG. 1 is a block diagram of the present remote ECG monitoring system.

Referring now to the drawings and, more particularly, to FIG. 1, there is shown a remote monitoring and telemetry system, generally designated 10, for use in a hospital 11 for simultaneously monitoring, at one or more central monitoring stations 12, ECG or other baseband information from one or more patients 13 located in rooms 14 scattered throughout hospital 11. The only requirement is that hospital 11 be equipped with a conventional master antenna television (MATV) cable system, generally designated 15, typically including a roof antenna 16 connected via a power amplifier 17 to a cable 18, which has a myriad of splitters and taps (not shown) so as to extend throughout hospital 11 to a plurality of wall taps 19 to which televisions 20 may be connected for receiving conventional television programs. System 10 combines telemetry plus two-way, coaxial cable communication techniques to communicate ECG or other patient information from patient 13 to monitors 43 positioned at station 12 or any other convenient location in hospital 11 where a wall tap 19 exists.

Broadly speaking, patient 13 is connected via a plurality of electrical leads 21 to a portable, battery-operated, rechargeable, patient sensor/transmitter unit 22 which, by virtue of being battery-operated, eliminates any possibility of electrical shock to patient 13. As will be described more fully with regard to FIG. 2, patient unit 22 includes a range switch 23 which permits adjustment of the gain of a differential amplifier 24 within unit 22 to accommodate different energy levels that come from different patients. Patient unit 22 also includes an indicator light 25 that blinks in synchronism with the heartbeat of patient 13. Light 25 may be adjusted not to blink if the heartbeat is too weak or if the sensitivity is turned too low, so as to serve as a convenient gauge for establishing the position of switch 23. Indicator light 25 may also be used to indicate when the battery in unit 22 is low and requires recharging.

Patient unit 22 derives the ECG information from patient 13 and transmits, via an antenna 26, a signal having a first frequency, which signal is modulated with the baseband information. Each patient unit 22 will have a different first frequency within the frequency band selected for patient units 22, as will be described more fully hereinafter.

The signal transmitted by antenna 26 is received by the antenna 30 of an AC powered, wall-mounted, receiver/demodulator/modulator unit 31 which is connected via a line 32 to television set 20 and by a line 33 to the MATV wall tap 19 in room 14. Unit 31 allows signals to come from master antenna wall tap 19 straight through to television set 20 without interfering with the normal operation thereof. Unit 31 also demodulates the signal received from antenna 30 to derive the baseband information and provides an output tap 34 for receipt of a conventional non-isolated ECG monitor for viewing of ECG information in room 14. Unit 31 also couples to MATV wall tap 19 a second signal having a second frequency, different from the first frequency of unit 22, and modulated with the ECG information. Each unit 31 will have a different second frequency within the frequency band selected for units 31, as will be described more fully hereinafter.

It is the nature of master antenna television cable systems that the most effective and direct path from each wall tap 19 is to the head end of cable 18, typically on the roof, where antenna 16 and amplifier 17 exist to bring television signals to hospital 11. Accordingly, system 10 includes a directional coupler 35 in cable 18, adjacent the output of amplifier 17, including a lead 36 connected to a converter/amplifier unit 37. Directional coupler 35 is a conventional item that directs signals on cable 18 to amplifier 17 or converter/amplifier unit 37, and vice versa, but signals will not be directly coupled between amplifier 17 and unit 37. In any event, unit 37 converts the received signals from units 31 to a different frequency band, amplifies the signals and couples a third set of signals back into cable 18 via directional coupler 35, the third signals being similar to the signals normally received by cable 18 from antenna 16. Therefore, the baseband information from all patient units 22 in room 14 and other rooms in hospital 11 is now on cable 18 is transmitted to all portions of hospital 11 where cable 18 goes. Thus, at central monitoring station 12, there is provided one or more receiver/demodulator units 40 which are coupled to wall tap 19 via a line 41. Each unit 40 receives and demodulates the signal from one of patient units 22 to derive the baseband information.

Figure 2:
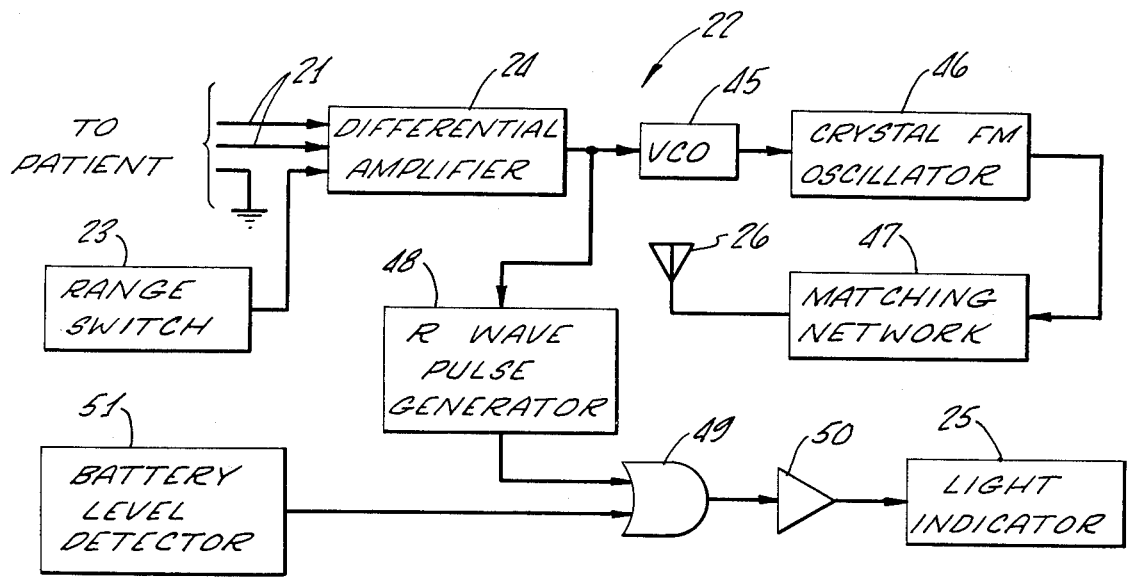
FIG. 2 is a block diagram of the patient sensor/transmitter unit of the system of FIG. 1.

Referring now to FIG. 2, patient unit 22 includes a differential amplifier 24 connected to patient 13 via leads 21 and a range switch 23 coupled to amplifier 24 for varying the sensitivity thereof. Range switch 23 permits adjustment of the gain of amplifier 24 to accommodate for the different energy levels that come from different patients. The use of a differential amplifier 24 provides common mode rejection and noise elimination. Thus, the output of differential amplifier 24 is a voltage analog of the hearbeat of patient 13. Such signal is applied to a voltage controlled oscillator 45 which provides a subcarrier signal having, for example, a center frequency of 2 kHz which is frequency modulated by the ECG analog.

The baseband signal from the patient 13 is in the frequency range of DC to 150 Hz and this signal is used to modulate the subcarrier provided by oscillator 45. The resultant output of oscillator 45 is a subcarrier signal having a frequency which is representative of the instantaneous voltage amplitude at the output of amplifier 24. The output of oscillator 45 is conducted to an FM oscillator 46 which is preferably crystal controlled to provide stability. The signal from oscillator 46 is frequency modulated by the output of oscillator 45 and applied via a matching network 47 to antenna 26.

Oscillator 46 preferably operates in the 174 to 216 MHz range, which is the frequency range established by the Federal Communications Commission for use in low power medical telemetry broadcasting. Providing a bandwidth of 200 kHz per channel, a hospital could be provided with a multiplicity of patient units 22 where the oscillators 46 therein are adjusted to 174 MHz, 174.2 MHz, etc., to provide a different frequency for each patient unit 22.

The signal from differential amplifier 24 is also processed within unit 22 to convert both positive and negative ECG pulses from patient 13 into uniform pulses, one per heartbeat, by an R wave pulse generator 48. The output of generator 48 is applied via an OR gate 49 and an amplifier 50 to indicator light 25, so that a nurse may take the pulse of patient 13 simply by watching the blinking of indicator light 25. A battery level detector 51 may also be connected to indicator light 25 via OR gate 49 so as to light indicator 25 permanently when the battery within unit 22 requires recharging.

Figure 3:
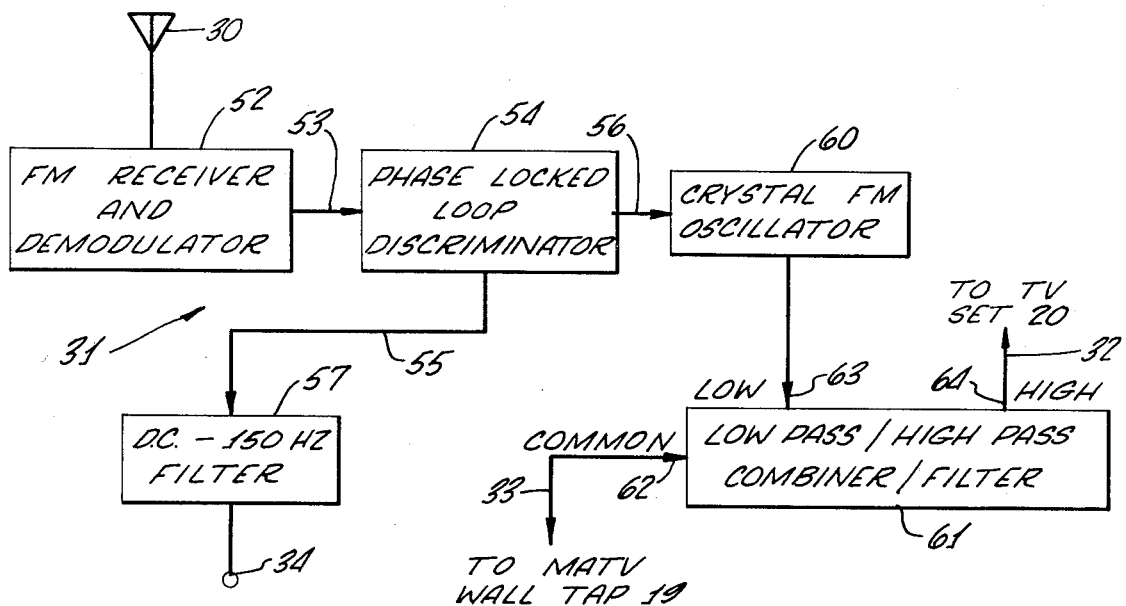
FIG. 3 is a block diagram of the receiver/demodulator unit of the system of FIG. 1.

Referring now to FIG. 3, the signal radiated by antenna 26 is received by antenna 30 of unit 31 mounted within room 14. The power of unit 22 and the sensitivity of unit 31 would be such as to permit freedom of movement of patient 13 within a range of approximately 100 feet without affecting the operation of system 10. Antenna 30 is coupled to a conventional FM receiver and demodulator 52 which is tuned to the specific frequency of oscillator 46, so that receiver 52 picks up signals only from patient unit 22 and not from other patient units 22. Receiver 52 demodulates the signal to provide, on an output line 53, the 2 kHz subcarrier, modulated by the baseband information from patient 13. Line 53 is connected to a phase locked loop discriminator 54 which recovers the baseband signal from the subcarrier signal on line 53.

A conventional phase locked loop discriminator has two outputs, here indicated as appearing on lines 55 and 56. The output on line 55 is the demodulated output signal which, in this case, is in the DC to 150 Hz range, which signal may be applied via a filter 57 to output tap 34, which is then available in room 14 for connection to a monitor to view the hearbeat of patient 13. The other output of discriminator 54, on line 56, is the same modulated subcarrier signal on line 53 which has been substantially filtered, since the frequency is eminating from a pure phase locked oscillator within discriminator 54. This recreated subcarrier signal, having the baseband information thereon, is applied to an FM oscillator 60, which is also preferably crystal controlled for purposes of stability. For present purposes, oscillator 60 is chosen to operate within the range of 18 to 24 megacycles, a frequency band which is high enough to conveniently pass through all of the network-type elements that exist in master antenna systems and yet low enough not to interfere with the normal broadcast channels. As was the case with patient unit 22, the oscillators 60 in different wall units 31 would be spaced in frequency by approximately 200 kHz so as to provide the required degree of separation between the channels of multiple units 31.

The output of oscillator 60 is applied to a low pass/high pass combiner/filter 61, a conventional off-the-shelf element having a common port 62, a low frequency port 63, and a high frequency port 64. If the output of oscillator 60 is applied to low frequency port 63, it emanates from common port 62, but not from high frequency port 64. Thus, by connecting common port 62 via line 33 to MATV wall tap 19, the output of oscillator 60 may be coupled directly to cable 18. The television signals coming down cable 18, on the other hand, which are at much higher frequencies and enter common port 62, emanate form high frequency port 64 where they may be connected via line 32 to television set 20. Thus, oscillator 60 will not interfere with the normal operation of television set 20.

Figure 4:
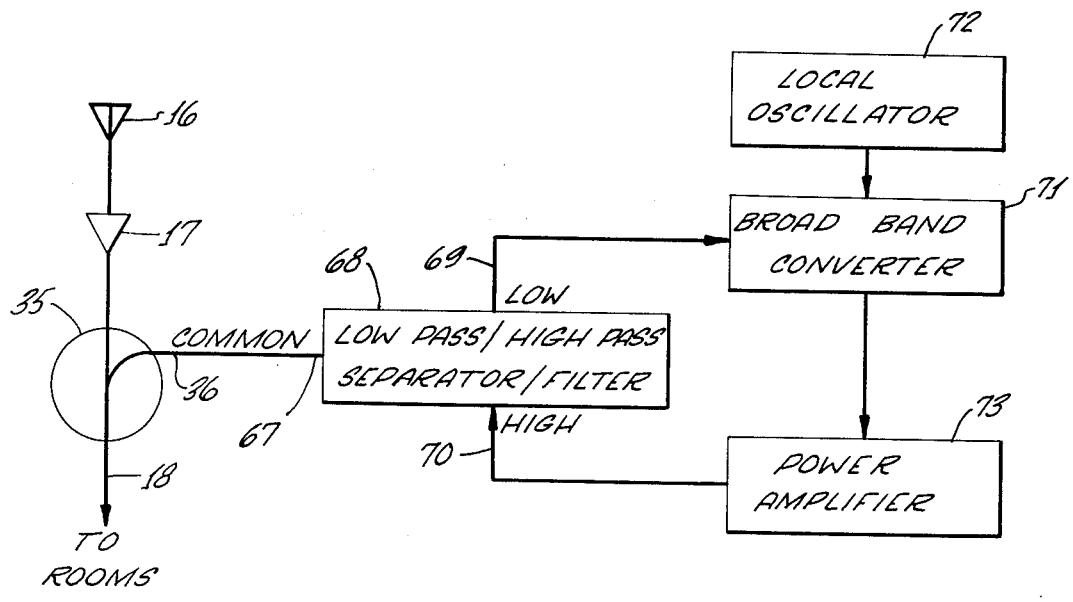
FIG. 4 is a block diagram of the converter/amplifier unit of the system of FIG. 1.

Referring now to FIG. 4, the signals from all oscillators 60, which have been applied to cable 18, appear at the head end of cable 18, at the output of amplifier 17. Cable 18, at the output of amplifier 17, is broken for insertion of directional coupler 35. The signals coming up cable 18 from all oscillators 60 are relatively weak and emanate into line 36 and the line connected to the output of amplifier 17. Since amplifier 17 is operating at a different frequency and since the signals are relatively weak, they do not affect the operation of amplifier 17.

The portion of the signals from cable 18 emanating on line 36 is applied to the common port 67 of a low pass/high pass separator/filter 68, which is identical to unit 61, and has a low frequency port 69 and a high frequency port 70. The low frequency signal entering common port 67 exits low frequency port 69 where it is conducted to a broadband converter 71, which also receives the signal from a local oscillator 72. Broadband converter 71 is a conventional device for receiving a band of frequencies and for converting them to a different band of frequencies, dependent upon the frequency of local oscillator 72. The result is that the signals applied to broadband converter 71, which may be 10, 20, 30, or more, frequencies confined within the 18 to 24 MHz range, exit from converter 71, converted, by way of example, to the 82 to 88 megacycle range. This frequency range is chosen because it corresponds to channel 6, which is an unassigned channel in the Los Angeles metropolitan area. Obviously, in different localities, the frequency of local oscillator 72 would be adjusted to utilize an available, unused channel.

The output of broadband converter 71 is applied to a power amplifier 73 where the signal strength is amplified and applied to high frequency port 70 of separator/filter 68. This high frequency signal finds its way back to common port 67 and then via lead 36 and directional coupler 35 back to cable 18. Power amplifier 73 adjusts the gain of the signal output from converter 71 so that it is now of a signal strength similar to what is currently emanating from amplifier 17 that is delivering the remaining channels of television to hospital 11.

Figure 5:
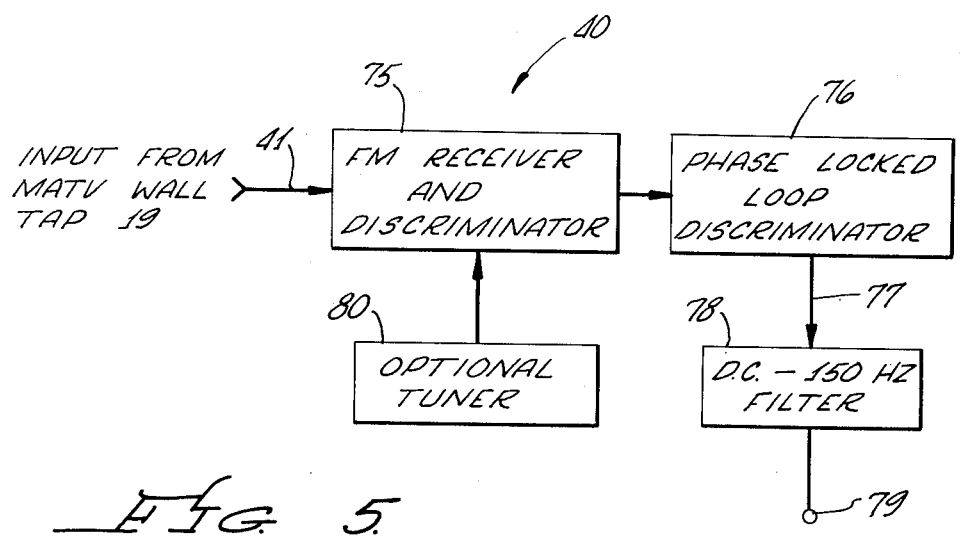
FIG. 5 is a block diagram of the receiver/demodulator unit of the system of FIG. 1.

Referring now to FIG. 5, the amplified signal from broadband converter 71 and amplifier 73 is now conducted throughout hospital 11 by cable 18. Therefore, the only thing left to be done is to receive it, and this may be done adjacent any MATV wall tap 19. Accordingly, at central monitoring station 12, line 41 is connected to wall tap 19 and then to a unit 40 which includes an FM receiver and discriminator 75, which is similar to FM receiver and demodulator 52, except that it is tuned to one of the frequencies from converter 71, the one that corresponds to the particular patient unit 22 desired. The output of receiver and discriminator 75, which is the subcarrier of 2 kHz, is conducted to a phase locked loop discriminator 76, which operates identically to discriminator 54 to provide the baseband information on a line 77 which is passed through a DC to 150 Hz filter 78 to an output tap 79. By connecting a conventional monitor 43 to tap 79, the ECG information from patient 13 may be viewed.

Assuming there were ten patients in hospital 11 provided with ten patient units 22 operating at ten different frequencies and ten wall units 31 operating at ten corresponding different frequencies, ten units 40 would be provided at central monitoring station 12 for simultaneously monitoring all patients 13. But in the cardiologist's office, or the like, it is not necessary to simultaneously monitor all patients. Therefore, the cardiologist's office may be provided with a single unit 40 having a tuner 80 coupled to FM receiver and discriminator 75. Tuner 80 would be similar to the tuner in a conventional television receiver. Under such circumstances, if the nurse at station 12 sees that patient numberr three is having a problem, she can call the cardiologist who can tune discriminator 75 to channel number three and immediately view the ECG information from patient number three. Or, if a patient was admitted to the emergency room and a problem occurred, the cardiologist could tune to the channel assigned to the emergency room and, from his office, view the problem there. By providing a channel in an operating room, the cardiologist could look in on a patient undergoing an operation without having to leave his office.

It can therefore be seen that according to the present invention, there is provided a remote ECG monitoring and telemetry system which solves the problems encountered heretofore. With the present system, each patient to be monitored is provided with a portable transmitter unit 22 which permits a certain freedom of movement in relation to the receiver unit 31 mounted in the patient's room 14. Unit 22 may have sufficient power and unit 31 may have sufficient sensitivity so that patient 13 can move around relatively freely, without affecting the signal from patient 13, provides an output plug 34 which is always available and adapted to receive a low-cost, non-isolated monitor which can be plugged in at any time to immediately view the patient's heartbeat, right in his room, without altering the connections to him.

After retransmission by unit 31 and conversion and amplification by unit 37, the information from all patients within hospital 11 is simultaneously available on cable 18. With such an arrangement, one can go to any wall tap 19 within hospital 11 and couple a receiver/demodulator unit 40 thereto to receive and demodulate the baseband information. Furthermore, multiple monitors can be provided in different locations in hospital 11 for monitoring by different personnel.

With system 10, a trained nurse or ECG observer can effectively monitor ECG and other patient information from widely scattered locations within hospital 11, at a single monitoring station. This being the case, it is unnecessary to put a patient in intensive care to monitor critical life support functions. When a patient is in trouble, the nurse knows exactly where he is and a portable monitor can be immediately attached to receiver unit 31 for monitoring instantaneous ECG information. System 10 can be installed in a conventional hospital without any rewiring or modification thereof, other than the installation of the various units and the connection thereof to the conventional master antenna wall taps 19.

While the invention has been described with respect to a preferred physical embodiment constructed in accordance therewith, it will be apparent to those skilled in the art that various modifications and improvements may be made without departing from the scope and spirit of the invention. For example, while specific frequency ranges have been given for the various units within system 10, by way of example only, it will be evident to those skilled in the art that a wide variety of frequency ranges may be used, depending on the circumstances and local transmitting regulations. Furthermore, while the present system has been described as applicable for the remote monitoring of patient ECG signals, it will be evident to those skilled in the art that the present system may be used to monitor other types of information. Accordingly, it is to be understood that the invention is not to be limited by the specific illustrative embodiment, but only by the scope of the appended claims.

I claim:

1. A remote monitoring and telemetry system for use in a facility equipped with a master antenna television cable comprising:
   means operatively coupled to a patient for deriving baseband information therefrom and for transmitting a first frequency signal modulated with said baseband information;
   means mounted in said facility in proximity to said patient for receiving said first modulated signal and for coupling to said master antenna television cable a second signal having a second frequency different from said first frequency and modulated with said baseband information;
   means coupled to said master antenna television cable adjacent the head end thereof for receiving said second modulated signal and for coupling to said master antenna television cable an amplified signal having a third frequency different from said first and second frequencies and modulated with said baseband information; and
   means coupled to said master antenna television cable for receiving and demodulating said third modulated signal to derive said baseband information.

2. A remote monitoring and telemetry system according to claim 1 wherein said first signal transmitting means includes first antenna means for radiating said first signal into the atmosphere and wherein said first signal receiving means includes second antenna means for receiving said radiated first signal.

3. A remote monitoring and telemetry system according to claim 1 wherein said first and third signals have frequencies within the frequency band normally associated wtih conventional television broadcasting.

4. A remote monitoring and telemtry system according to claim 1 wherein said baseband information is patient ECG information.

5. A remote monitoring and telemetry system according to claim 1 further comprising:
   a plurality of said patient baseband information deriving means operatively coupled to a plurality of different patients for transmitting first modulated signals having different frequencies within a first band of frequencies;
   a plurality of said first signal receiving means mounted in said facility in close proximity to said different patients for selectively receiving the different first signals in said first band of frequencies and for coupling to said master antenna television cable a plurality of second modulated signals having different frequencies within a second frequency band;
   wherein said second modulated signal receiving means receives all of said second signals within said second frequency band and couples to said master antenna television cable a plurality of amplified signals having different frequencies in a third frequency band and modulated with said baseband information from said different patients; and
   a plurality of said third modulated signal receiving and demodulating means coupled to said master antenna television cable and tuned to said different frequencies in said third frequency band for deriving said baseband information from said different patients.

6. A remote monitoring and telemetry system according to claim 1 wherein said first signal transmitting means comprises:
   means for deriving said baseband information from said patient;
   means for generating said first frequency signal;
   means for modulating said first frequency signal with said baseband information; and
   antenna means for radiating said first modulated signal.

7. A remote monitoring and telemtry system according to claim 6 wherein said modulating means frequency modulates said first signal with said base band information.

8. A remote monitoring and telemetry system according to claim 6 wherein said baseband information is ECG information of a patient and wherein said first signal transmitting means further comprises:
   means responsive to said ECG information for generating a pulse for each heartbeat of said patient; and
   visual indicator means for displaying said heartbeat pulses.

9. A remote monitoring and telemetry system according to claim 1 wherein said first signal receiving means comprises:
   means for receiving and demodulating said first modulated signal to derive a signal containing said baseband information;
   means for generating said second frequency signal;
   means for modulating said second frequency signal with said derived signal containing said baseband information; and
   means for coupling said second modulated signal to said master antenna television cable.

10. A remote monitoring and telemetry system according to claim 9 wherein said second modulating means frequency modulates said second signal with said signal containing said baseband information.

11. A remote monitoring and telemtry system according to claim 9 wherein said first modulated signal receiving means further comprises:
   output terminal means coupled to said receiving and demodulating means for providing said baseband information for access to an external monitor.

12. A remote monitoring and telemetry system according to claim 9 wherein said means for coupling said second modulated signal to said master antenna television cable comprises:
   a low pass/high pass combiner/filter having a common port, a low frequency port, and a high frequency port, said master antenna television cable being connected to said common port, said second moduluated signal being coupled to one of said low or high frequency ports, the other of low or high frequency ports being connectible to a conventional television receiver for receipt of television signals from said master antenna television cable.

13. A remote monitoring and telemetry system according to claim 1 wherein said second modulated signal receiving means comprises:

a directional coupler positioned in said master antenna television cable for receiving said second modulated signal but not receiving signals normally received by the antenna of said master antenna television cable;

means operatively coupled to said directional coupler for converting said second modulated signal to a third modulated signal having a frequency different from said second frequency; and means for amplifying said third modulating signal, said amplified third modulated signal being applied to said directional coupler for application to said master antenna television cable.

14. A remote monitoring and telemetry system according to claim 13 wherein said second modulated signal receiving means further comprises:

a low pass/high pass separator/filter having a common port, a low frequency port, and a high frequency port, said common port being connected to said directional coupler, one of said low or high frequency ports being connected to said second modulated signal converting means, the other of said low or high frequency ports being connected to the output of said amplifying means.

15. A remote monitoring and telemetry system according to claim 13 wherein said amplifying means amplifies said third signal to a level having the same general magnitude as the conventional television broadcast signals received by said master antenna television cable.

16. A remote monitoring and telemetry system according to claim 15 wherein said third signal has a frequency within the frequency band normally associated with conventional television broadcasting.

17. A remote monitoring and telemetry system according to claim 13 wherein said third modulated signal receiving and demodulating means comprises:

output terminal means providing said baseband information for access to an external monitor.

18. A remote monitoring and telemetry system for use in a facility equipped with a master antenna television cable system comprising:

a patient unit comprising:
means for deriving baseband information from a patient;
means for generating a first frequency signal;
means for modulating said first frequency signal with said baseband information; and
antenna means for transmitting said first modulated signal;

a receiver/retransmitter unit comprising:
means for receiving and demodulating said first modulated signal to derive a signal containing said baseband information;
means for generating a second frequency signal different from said first frequency signal;
means for modulating said second frequency signal with said derived signal containing said baseband information; and
means for coupling said second modulated signal to said master antenna television cable;

a converter/amplifier unit positioned adjacent the head end of said master antenna television cable comprising:
means coupled to said master antenna television cable for receiving said second modulated signal;
means operatively coupled to said receiving means for converting said second modulated signal to a third modulated signal having a frequency different from said second frequency;
means for amplifying said third modulated signal; and
means for coupling said amplified third modulated signal to said master antenna television cable; and a monitoring unit comprising:
means coupled to said master antenna television cable for receiving and demodulating said third modulated signal to derive said baseband information.

19. A remote monitoring and telemetry system according to claim 18 wherein said first and third signals have frequencies within the frequency band normally associated with conventional television broadcasting.

20. A remote monitoring and telemetry system according to claim 18 wherein said baseband information is patient ECG information.

21. A remote monitoring and telemetry system according to claim 18 further comprising:

a plurality of said patient units operatively coupled to a plurality of different patients for transmitting first modulated signals having different frequencies within a first band of frequencies;

a plurality of said receiver/retransmitter units for selectively receiving the different first signals in said first band of frequencies for coupling to said master antenna television cable a plurality of second modulated signals having different frequencies within a second frequency band;

wherein said converter/amplifier unit receives all of said second signals within said second frequency band and couples to said master antenna television cable a plurality of amplified signals having different frequencies in a third frequency band and modulated with said baseband information from said different patients; and a plurality of said monitoring units coupled to said master antenna television cable and tuned to said different frequencies in said third frequency band for deriving said baseband information from said different patients.

22. A remote monitoring and telemetry system according to claim 21 further comprising:

a tuneable monitoring unit coupled to said master antenna television cable and selectively tuneable to one of said different frequencies in said third frequency band for deriving said baseband information from a selected patient.

23. A remote monitoring and telemetry system according to claim 18 wherein said baseband information is ECG information of said patient and wherein said patient unit further comprises:

means responsive to said ECG information for generating a pulse for each heartbeat of said patient; and
visual indicator means for displaying said heartbeat pulses.

24. A remote monitoring and telemetry system according to claim 18 wherein said receiver/retransmitter unit further comprises:

output terminal means coupled to said receiving and demodulating means for providing said baseband information for access to an external monitor.

25. A remote monitoring and telemetry system according to claim 18 wherein said means for coupling said second modulated signal to said master antenna television cable comprises:

a low pass/high pass combiner/filter having a common port, a low frequency port, and a high frequency port, said master antenna television cable being connected to said common port, said second modulated signal being coupled to one of said low or high frequency ports, the other of said low or high frequency ports being connectible to a conventional television receiver for receipt of teleision signals from said master antenna television cable, and wherein said converter/amplifier unit further comprises:

a low pass/high pass separator/filter having a common port, a low frequency port, and a high frequency port, said common port being connected to said directional coupler, one of said low or high frequency ports being connected to said second modulated signal converting means, the other of said low or high frequency ports being connected to the output of said amplifying means.

26. A remote monitoring and telemetry system according to claim 18 wherein said amplifying means amplifies said third signal to a level having the same general magnitude as the conventional television broadcast signals received by said master antenna television cable.

27. A remote monitoring and telemetry system according to claim 18 wherein said monitoring unit further comprises:

output terminal means providing said baseband information for access to an external monitor.

* * * * *